United States Patent
Loeffler et al.

(10) Patent No.: US 7,553,495 B2
(45) Date of Patent: *Jun. 30, 2009

(54) LIQUID COMPOSITIONS COMPRISING OXYALKYLATED POLYGLYCEROL ESTERS

(75) Inventors: Matthias Loeffler, Niedernhausen (DE); Peter Klug, Großostheim (DE); Franz-Xaver Scherl, Burgkirchen (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/940,840

(22) Filed: Sep. 14, 2004

(65) Prior Publication Data

US 2005/0112081 A1    May 26, 2005

(30) Foreign Application Priority Data

Sep. 15, 2003    (DE)    ................ 103 42 870

(51) Int. Cl.
*A61K 9/00* (2006.01)
*A61K 8/02* (2006.01)

(52) U.S. Cl. .................. 424/400; 424/401; 514/941

(58) Field of Classification Search ................ 424/400, 424/401; 514/941
See application file for complete search history.

(56) References Cited

U.S. PATENT DOCUMENTS

| | | | | |
|---|---|---|---|---|
| 2,679,520 | A | | 5/1954 | de Groote |
| 4,265,774 | A | * | 5/1981 | Langdon ................ 508/579 |
| 4,522,740 | A | * | 6/1985 | Schmid et al. ............ 510/219 |
| 4,614,622 | A | | 9/1986 | Huettinger et al. |
| 4,636,525 | A | * | 1/1987 | Ochiai et al. ............ 514/786 |
| 4,774,017 | A | | 9/1988 | Seibert |
| 4,853,026 | A | | 8/1989 | Frisch et al. |
| 4,895,681 | A | * | 1/1990 | Herrmann et al. ......... 554/223 |
| 4,977,030 | A | | 12/1990 | Hotta et al. |
| 5,026,800 | A | | 6/1991 | Kimura et al. |
| 5,142,036 | A | * | 8/1992 | Akimoto et al. .......... 536/18.3 |
| 5,192,462 | A | | 3/1993 | Gloor et al. |
| 5,597,551 | A | | 1/1997 | Malawer et al. |
| 5,750,468 | A | | 5/1998 | Wright et al. |
| 5,858,921 | A | | 1/1999 | Magin et al. |
| 5,912,208 | A | | 6/1999 | Hioki |
| 5,994,415 | A | * | 11/1999 | Gruning et al. ........... 516/116 |
| 6,306,410 | B1 | * | 10/2001 | Doki ..................... 424/401 |
| 6,368,581 | B1 | | 4/2002 | Karlen et al. |
| 2003/0235598 | A1 | * | 12/2003 | Klug et al. .............. 424/401 |
| 2004/0072916 | A1 | * | 4/2004 | Leinweber et al. ........ 516/135 |
| 2004/0143057 | A1 | | 7/2004 | Ahrens et al. |
| 2005/0037926 | A1 | | 2/2005 | Zerrer |
| 2006/0166826 | A1 | | 7/2006 | Zerrer et al. |
| 2006/0264330 | A1 | | 11/2006 | Zerrer et al. |

FOREIGN PATENT DOCUMENTS

| | | |
|---|---|---|
| CA | 2 451 237 | 1/2003 |
| DE | 20 24 051 A1 | 12/1971 |
| DE | 32 39 564 C1 | 5/1984 |
| DE | 34 46 720 A1 | 6/1986 |
| DE | 37 26 015 | 2/1988 |
| DE | 195 05 178 A1 | 8/1996 |
| DE | 199 36 092 A1 | 2/2001 |
| DE | 101 24 547 | 11/2002 |
| DE | 10211801 A1 * | 10/2003 |
| EP | 0 264 826 | 4/1988 |
| EP | 0 349 240 | 1/1990 |
| EP | 0 379 852 | 8/1990 |
| EP | 1 055 407 A | 11/2000 |
| EP | 1 344 518 A2 | 9/2003 |
| GB | 1 333 475 | 10/1973 |
| JP | 54 163984 | 6/1978 |
| JP | 58 196258 | 2/1984 |
| JP | 60 212480 | 10/1985 |
| JP | 61 130208 A | 6/1986 |
| JP | 2001 139796 | 9/2001 |
| WO | WO 96/025215 | 8/1996 |
| WO | WO 98/006259 | 2/1998 |
| WO | WO 99/005914 | 2/1999 |
| WO | WO 01/008481 | 1/2001 |
| WO | WO 200108481 A1 * | 2/2001 |
| WO | WO 02/089575 | 11/2002 |
| WO | WO 03/000055 | 1/2003 |
| WO | WO 03/063818 | 8/2003 |

OTHER PUBLICATIONS

English abstract for DE 101 24 547, Nov. 28, 2002.
English abstract for DE 195 05 178 A1, Aug. 22, 1996.
English abstract for DE 34 46 720 A1, Jun. 26, 1986.
English abstract for JP 54 163984, Jun. 16, 1978.
English abstract for JP 58 196258, Feb. 15, 1984.
English abstract for JP 60 212480, Oct. 24, 1985.
English abstract for JP 61 130208 A, Jun. 18, 1986.
English abstract for JP 2001 139796, Sep. 3, 2001.
English abstract for WO 96/25215, Aug. 22, 1996.
English abstract for WO 01/08481, Jan. 8, 2001.
English abstract for WO 03/063818, Aug. 7, 2003.
English abstract for DE 199 36 092 A1, Feb. 1, 2001.
EPO Search Report for EP 04 02 0723, dated Mar. 30, 2006.

* cited by examiner

*Primary Examiner*—Sreeni Padmanabhan
*Assistant Examiner*—Renee Claytor
(74) *Attorney, Agent, or Firm*—Tod A. Waldrop

(57) ABSTRACT

Compositions are described which comprise oxyalkylated polyglycerol esters, one or more organic solvents and water. The compositions are exceptionally suitable for the thickening of surfactant-containing systems.

9 Claims, No Drawings

LIQUID COMPOSITIONS COMPRISING OXYALKYLATED POLYGLYCEROL ESTERS

Consumer wishes and rheology of cosmetic products are closely related. Thus, for example, the visual appearance of a cream or lotion is influenced by the viscosity. The sensory properties, such as consistency or spreadability, determine the individual profile of a cosmetic product. The effectiveness of active substances (e.g. sunscreen filters) and the storage stability of the formulation are also closely related to the Theological properties of the product. In the cosmetics sector, the thickeners and gel formers therefore play a major role.

A number of patent specifications describe the use of polyether esters as thickeners. The use of long-chain polyethers with fatty acid ester radicals, for example of polyethylene glycol 6000 distearate (PEG 6000 distearate) is prior art. U.S. Pat. No. 4,774,017 describes polyethylene glycol polypropylene glycol monoethers as consistency-imparting component, and DE 37 26 015 describes the reaction products of polyalcohols with fatty acids, for example pentaerythritol fatty acid esters, and their thickening effect. U.S. Pat. No. 5,129,462 describes shampoo formulations comprising polyethylene glycol polyol fatty acid esters, in particular PEG pentaerythritol fatty acid esters, as thickeners.

The processing and formulability of this class of compound is adversely affected by their high melting points or setting points. If solid thickeners are used in the production of surfactant-containing cosmetic products, such as, for example, a shampoo or shower bath, it is necessary to work at elevated temperature. This means that the entire surfactant/water/thickener mixture has to be heated in order to dissolve or melt the solid thickener. The mixture then has to be cooled again to room temperature. This operation is disadvantageous for time and cost reasons.

The object was therefore to provide thickeners which are present in liquid form and can thus be incorporated into formulations in a simple manner. Additionally, a high active content (solids content) is advantageous. Furthermore, at room temperature, these liquid thickener concentrates should have a homogeneous appearance which is as clear as possible, and have no sedimentations or inhomogeneities of any kind even upon prolonged storage at low or high temperatures.

Surprisingly, it has been found that the wax-like oxyalkylated polyglycerol esters of the formula (1)

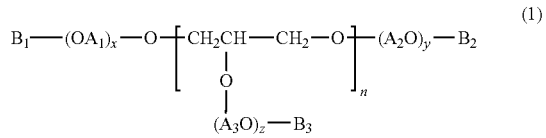

in which
$A_1$, $A_2$ and $A_3$ independently of one another are in each case a group of the formula —$C_2H_4$— or —$C_3H_6$—,
$B_1$, $B_2$ and $B_3$ independently of one another are in each case hydrogen or a group of the formula —COR, where at least one of the radicals $B_1$, $B_2$ or $B_3$ is a group of the formula —COR,
R is $C_7$-$C_{21}$-alkyl, $C_7$-$C_{21}$-hydroxyalkyl or $C_2$-$C_{21}$-alkenyl,
n is on average a number from 1.5 to 10, and
x, y and z are numbers from 0 to 100, where the sum of x, y and z is 50 to 250,
can be provided in a highly concentrated liquid form with a clear appearance if they are dissolved in a mixture of water and organic solvent or water and organic solvent mixture.

The invention provides flowable compositions or concentrates, in particular thickener concentrates, comprising
a) one or more oxyalkylated polyglycerol esters of the formula (1)

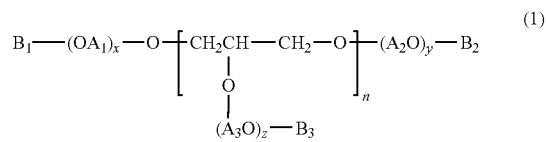

in which
$A_1$, $A_2$ and $A_3$ independently of one another are in each case a group of the formula —$C_2H_4$— or —$C_3H_6$—,
$B_1$, $B_2$ and $B_3$ independently of one another are in each case hydrogen or a group of the formula —COR, where at least one of the radicals $B_1$, $B_2$ or $B_3$ is a group of the formula —COR,
R is $C_7$-$C_{21}$-alkyl, $C_7$-$C_{21}$-hydroxyalkyl or $C_2$-$C_{21}$-alkenyl,
n is on average a number from 1.5 to 10, preferably from 1.8 to 5, and
x, y and z are numbers from 0 to 100, where the sum of x, y and z is 50 to 250, preferably from 100 to 200, in particular from 130 to 170,
b) an organic solvent or organic solvent mixture, and
c) water.

The numbers given for the degree of condensation n are number-average values.

The compositions according to the invention comprise an organic solvent or an organic solvent mixture.

In principle, suitable organic solvents are all mono- or polyhydric alcohols or derivatives of mono- or polyhydric alcohols, provided that they are different from the compounds of the formula (1). Among the derivatives of the mono- and polyhydric alcohols, preference is given to esters and ethers.

In a preferred embodiment, the compositions according to the invention comprise at least one monohydric alcohol as organic solvent.

Preferred monohydric alcohols which can be used in the compositions according to the invention as solvent are chosen from the group consisting of methanol, ethanol, propanol, isopropanol, n-butanol, isobutanol, t-butanol, hexyl alcohol, trimethylhexanol, butyloctanol, fatty alcohols, preferably myristyl, cetyl, oleyl and stearyl alcohol, benzyl alcohol, phenylpropanol and diacetone alcohol.

In a further preferred embodiment, the compositions according to the invention comprise at least one polyhydric alcohol or a derivative of a polyhydric alcohol as organic solvent.

Preferred polyhydric alcohols and derivatives of polyhydric alcohols which can be used in the compositions according to the invention as solvent are chosen from the group consisting of methoxyethanol, ethoxyethanol, butoxyethanol, isobutoxypropanol, methoxyisopropanol, butoxyisopropanol, phenoxyisopropanol, methoxybutanol, preferably 4-methoxybutanol, methoxymethylbutanol, glycol, benzene glycol, propylene glycol, butylene glycol, butanediol, methylpropanediol, pentylene glycol, isopentyldiol, neopentyl glycol, hexylene glycol, hexanediol, ethylhexanediol, diethylene glycol, methoxy diglycol, ethoxy diglycol, butoxy diglycol, dimethoxy diglycol, dipropylene glycol, glycerol and 1,2,6-hexanetriol.

In a further preferred embodiment, the compositions according to the invention comprise at least one derivative of a mono- or polyhydric alcohol chosen from ethoxylated and/or propoxylated alcohols as solvent. Among these derivatives, preference is given to ethoxylated and/or propoxylated alcohols having 1 to 40 mol, preferably 1 to 30 mol, particularly preferably 1 to 20 mol, of ethylene oxide and/or propylene oxide per 1 mol of the parent mono- or polyhydric alcohol. Particular preference is given to polypropylene glycol-7 and polypropylene glycol-10.

In a further preferred embodiment, the compositions according to the invention comprise at least one organic solvent based on vegetable oils or based on mono-, di- or triglycerides, i.e. compounds based on glycerol and fatty acids, or based on mixtures of these glycerides. In particular, ethoxylated and/or propoxylated, preferably ethoxylated, derivatives of mono-, di- or triglycerides, which also include those compounds in which ethylene oxide and/or propylene oxide units may be located between the glycerol units and the acid units, or mixtures of these glycerides, which are additionally liquid at room temperature, are exceptionally suitable as solvents. In a particularly preferred embodiment, however, the ethoxylated and/or propoxylated derivatives of the mono-, di- and triglycerides contain no ethylene oxide and/or propylene oxide units between the glycerol units and the acid units.

In a further preferred embodiment, the compositions according to the invention comprise, as solvent, at least one derivative of monoglycerol, in which a polyalkylene glycol radical which is made up of ethylene oxide and/or propylene oxide units, preferably ethylene oxide units, is bonded via an ether bridge to one, two or three of the hydroxyl groups of the monoglycerol, and where these derivatives contain between 1 and 40 mol, preferably between 1 and 30 mol and particularly preferably between 1 and 20 mol, of alkylene oxide per 1 mol of monoglycerol, and where one, two or three of the hydroxyl groups of these compounds are esterified, and the ester radicals are derived from saturated, unsaturated, straight-chain or branched carboxylic acids having 6 to 22 carbon atoms. Further preferably, the solvent consists of a mixture of the monoglycerol derivatives just mentioned.

In a further preferred embodiment, the compositions according to the invention comprise, as solvent, at least one derivative of monoglycerol, where one, two or three of the hydroxyl groups of the monoglycerol are esterified and the ester radicals are derived from saturated, unsaturated, straight-chain or branched carboxylic acids having 6 to 22 carbon atoms, in which a polyalkylene glycol radical, which is made up of ethylene oxide and/or propylene oxide units, preferably ethylene oxide units, is bonded via an ether bridge to one or two of the nonesterified hydroxyl groups of monoglycerol, and where these derivatives contain between 1 and 40 mol, preferably between 1 and 30 mol and particularly preferably between 1 and 20 mol of alkylene oxide per 1 mol of monoglycerol. Further preferably, the solvent consists of a mixture of the monoglycerol derivatives just mentioned.

In a further preferred embodiment, the compositions according to the invention comprise, as solvent, at least one compound of the formula (1) but in which n is 1 and the sum of x, y and z is 1 to 40, preferably 1 to 30 and particularly preferably 1 to 20. These compounds are referred to below as compounds of the formula (2).

Among the derivatives of glycerol as solvent, particular preference is given to PEG-6 caprylic/capric glycerides (e.g. Softigen 767, Sasol), i.e. polyethylene glycol derivates of a mixture of mono-, di- and triglycerides of caprylic and capric acids with, on average, 6 mol of ethylene oxide and PEG-7 glyceryl cocoate (e.g. Cetiol HE, Cognis), i.e. a polyethylene glycol ether of glyceryl cocoate with, on average, 7 mol of ethylene oxide per 1 mol of glycerol.

The oxyalkylated polyglycerol esters according to formula (1) are prepared either by oxyalkylation of a polyglycerol and subsequent esterification, or by esterification of the polyglycerol and subsequent oxyalkylation.

The alkoxylated polyglycerol esters used according to the invention are prepared in two or more reaction stages. The synthesis of the polyglycerols or oligoglycerols, diglycerol, triglycerol, tetraglycerol to decaglycerol takes place in a known manner by polycondensation of glycerol in the presence of catalysts, for example reducing phosphoric acids, alkali metal hydroxides, alkali metal carbonates, alkali metal bicarbonates, alkali metal alcoholates and alkoxides at temperatures of from 190 to 270° C. With the discharge of water of condensation, the formation of the polyglycerols takes place within 8 to 72 hours. The hydroxyl number (OH number) of such a reaction mixture is, for example, 1072 mg of KOH/g for an oligomer mixture, which corresponds, on average, to a polyglycerol-4. The number n, being a measure of the degree of condensation, is between 1.5 and 10, in particular between 1.8 and 5.

The alkoxylation, in particular the ethoxylation, of the polyglycerols or oligoglycerols takes place at 130 to 190° C., preferably at 160° C., in the presence of a basic catalyst, for example NaOH, after drying at 100° C. and a vacuum of 20 mbar (about 0.5 hours), where alkoxide, preferably ethylene oxide, is metered in at a pressure of from 1 to 6 bar, in particular 4 to 6 bar, in the course of 15 hours. The resulting ethoxylated polyglycerols or oligoglycerols have a total degree of EO (x+y+z) of from 50 to 250, preferably 100 to 200, particularly preferably 130 to 170, based on the average molecular mass of the polyglycerol.

The prepared ethoxylated poly/oligoglycerol is, after cooling the reaction mixture to 60 to 100° C., treated with a catalyst, e.g. alkylbenzenesulfonic acid, and the pH is adjusted to 4 to 5 (10% aqueous) by adding acid, preferably hypophosphorous acid or phosphoric acid. Esterification is then carried out by adding a fatty acid, for example stearic acid, isostearic acid, 12-hydroxystearic acid, coconut fatty acid, lauric acid, oleic acid or alkyl esters thereof, chlorides or anhydrides at a reaction temperature of from 160 to 230° C. and a reaction time of from 10 to 35 hours. The molar fraction of fatty acid or fatty acid derivative can be chosen as desired, but at least one OH group of the oxyalkylated polyglycerol must be esterified.

The preparation method for these alkoxylated poly/oligoglycerol fatty acid esters can also be varied such that the poly/oligoglycerols are firstly esterified with fatty acid in the corresponding molar ratio and then alkoxylated.

As a result of this preparation process, the polyglycerol derivatives are mixtures of compounds of the abovementioned formula with a varying value for n, i.e. mixtures with a content of monoglycerol ester are also suitable.

The abovementioned alkoxylated polyglycerol esters are predominantly waxes at room temperature which, with a mixture of water and organic solvent or water and organic solvent mixture, produce the flowable, easy-to-handle products with a clear appearance according to the invention. The (optionally heated) solvents are advantageously added directly to the molten alkoxylated polyglycerol esters, preferably at 60 to 100° C., particularly preferably at 80° C.

The present invention thus also further provides the use of an oxyalkylated polyglycerol ester of the formula (1), at least one organic solvent or an organic solvent mixture and water for the preparation of the compositions according to the invention.

Attempts to dissolve the wax-like alkoxylated polyglycerol esters of the formula (1) into water or into anhydrous organic solvents led to unsatisfactory results. The solutions were inhomogeneous with a cloudy appearance (see table 1).

TABLE 1

(data in % by weight)

|  | A | B | C | D | E |
|---|---|---|---|---|---|
| Thickener | 60 | 60 | 60 | 60 | 60 |
| Demin. water | 40 | 20 | — | — | 30 |
| Cetiol HE | — | 20 | 40 | — | — |
| Softigen 767 | — | — | — | 40 | 10 |
| Appearance | 1 | 2 | 3 | 3 | 2 |

1: cloudy, high viscosity;
2: clear, low viscosity;
3: flocculation, solid

The thickener used in the experiments shown in table 1 was diglycerol-148 EO tristearate, i.e. a compound according to formula (1), in which n=2, $A=C_2H_4$, x+y+z=about 148 and B=stearyl.

Description of the experiment:

The diglycerol-148 EO tristearate is heated to 80° C. The solvent is then added in an amount corresponding to the percentages by weight given in table 1. The resulting solution is then cooled to room temperature.

Chemical name of the commercial products used:
Cetiol HE: PEG-7 glyceryl cocoate
Softigen 767: PEG-6 caprylic/capric glyceride The compositions according to the invention comprise, based on the total composition, 10 to 95% by weight, preferably 20 to 80% by weight and particularly preferably 30 to 70% by weight, of alkoxylated polyglycerol acid esters of the formula (1).

In the compositions according to the invention, the weight ratio of water to organic solvent or organic solvent mixture is preferably from 3:1 to 1:3.

The compositions according to the invention are suitable as thickeners and dispersants for aqueous, aqueous-alcoholic and aqueous-surface-active preparations and as emulsifiers or suspending agents with a thickening action and consistency-imparting agent for emulsions and suspensions. In particular, they are suitable as thickeners in surfactant-containing systems.

The invention therefore also further provides the use of a composition according to the invention as thickener in surfactant-containing systems.

The preparations, emulsions and suspensions comprising a composition according to the invention are cosmetic, dermatological and pharmaceutical products.

The present invention therefore also further provides the use of a composition according to the invention for the preparation of a cosmetic, dermatological or pharmaceutical product, and also a cosmetic, dermatological or pharmaceutical product comprising a composition according to the invention.

Preferably, the cosmetic, dermatological or pharmaceutical products are in the form of shampoos, shower baths, shower gels, foam baths, gels, lotions, creams or ointments.

The cosmetic, dermatological or pharmaceutical products according to the invention comprise, based on the finished formulation, preferably 0.05 to 10% by weight, particularly preferably 0.1 to 5% by weight, especially preferably 0.5 to 3% by weight of the polyglycerol esters of the formula (1).

The cosmetic, dermatological or pharmaceutical products according to the invention can comprise, as further auxiliaries and additives, all customary anionic, cationic, zwitterionic, nonionic and amphoteric surfactants, and further additives customary in cosmetics, such as, for example, superfatting agents, stabilizers, biogenic active ingredients, glycerol, preservatives, pearlizing agents, dyes and fragrances, solvents, opacifiers, further thickeners and dispersants, and also protein derivatives, such as gelatin, collagen hydrolyzates, natural- and synthetic-based polypeptides, egg yolk, lecithin, lanolin and lanolin derivatives, fatty alcohols, silicones, deodorizing agents, substances with a keratolytic and keratoplastic effect, enzymes and carrier substances. In addition, antimicrobially effective agents may be added to the cosmetic, dermatological or pharmaceutical products according to the invention.

The total amount of surfactants used in the cosmetic, dermatological or pharmaceutical products according to the invention can, based on the finished product, be between 5 and 70% by weight, preferably between 10 and 40% by weight, particularly preferably between 12 and 35% by weight, based on 100% of active substance.

Anionic washing-active substances which may be mentioned are: $(C_{10}-C_{20})$-alkyl carboxylates and alkylene carboxylates, alkyl ether carboxylates, fatty alcohol sulfates, fatty alcohol ether sulfates, alkylamide sulfates and -sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates and acyl glutamates. These compounds and their mixtures are used in the form of their water-soluble or water-dispersible salts, for example the sodium, potassium, magnesium, ammonium, mono-, di- and triethanolammonium salts, and analogous alkylammonium salts.

The proportion by weight of the anionic surfactants in the cosmetic, dermatological or pharmaceutical products according to the invention is preferably in the range from 7 to 30% by weight, particularly preferably 10 to 25% by weight, especially preferably 12 to 22% by weight.

Suitable cationic surfactants are, for example, quaternary ammonium salts, such as di$(C_{10}-C_{24})$-alkyldimethylammonium chloride or bromide, preferably di$(C_{12}-C_{18})$-alkyldimethylammonium chloride or bromide; $(C_{10}-C_{24})$-alkyldimethylethylammonium chloride or bromide; $(C_{10}-C_{24})$-alkyltrimethylammonium chloride or bromide, preferably cetyltrimethylammonium chloride or bromide and $(C_{20}-C_{22})$-alkyltrimethylammonium chloride or bromide; $(C_{10}-C_{24})$-alkyldimethylbenzylammonium chloride or bromide, preferably $(C_{12}-C_{18})$-alkyldimethylbenzylammonium chloride; N—$(C_{10}-C_{18})$-alkylpyridinium chloride or bromide, preferably N-$(C_{12}-C_{16})$-alkylpyridinium chloride or bromid; N—$(C_{10}-C_{18})$-alkylisoquinolinium chloride, bromide or monoalkyl sulfate; N—$(C_{12}-C_{18})$-alkylpolyoylaminoformylmethylpyridinium chloride; N—$(C_{12}-C_{18})$-alkyl-N-methylmorpholinium chloride, bromide or monoalkyl sulfate; N—$(C_{12}-C_{18})$-alkyl-N-ethylmorpholinium chloride, bromide or monoalkyl sulfate; $(C_{16}-C_{18})$-alkylpentaoxethylammonium chloride; diisobutylphenoxyethoxyethyidimethylbenzylammonium chloride; salts of N,N-diethylaminoethylstearylamide and -oleylamide with hydrochloric acid, acetic acid, lactic acid, citric acid, phosphoric acid; N-acylaminoethyl-N, N-diethyl-N-methylammonium chloride, bromide or monoalkyl sulfate and N-acylaminoethyl-N, N-diethyl-N-benzylammonium chloride, bromide or monoalkyl sulfate, where acyl is preferably stearyl or oleyl.

The proportion by weight of the cationic surfactants in the cosmetic, dermatological or pharmaceutical products according to the invention is preferably in the range from 1 to 10% by weight, particularly preferably 2 to 7% by weight, especially preferably 3 to 5% by weight.

Examples of suitable nonionic surfactants are: fatty alcohol ethoxylates (alkyl polyethylene glycols); alkylphenol polyethylene glycols; alkyl mercaptan polyethylene glycols; fatty amine ethoxylates (alkylaminopolyethylene glycols); fatty acid ethoxylates (acyl polyethylene glycols); polypropylene glycol ethoxylates (Pluronics®); fatty acid alkylolamides, (fatty acid amide polyethylene glycols); N-alkyl-, N-alkoxypolyhydroxy fatty acid amide, sucrose esters; sorbitol esters and polyglycol ethers.

The proportion by weight of the nonionic surfactants in the cosmetic, dermatological or pharmaceutical products according to the invention is preferably in the range from 1 to 20% by weight, particularly preferably 2 to 10%, especially preferably 3 to 7% by weight.

Preferred amphoteric surfactants are: N—($C_{12}$-$C_{18}$)-alkyl-β-aminopropionates and N—($C_{12}$-$C_{18}$)-alkyl-β-iminodipropionates as alkali metal and mono-, di- and trialkylammonium salts; N-acylaminoalkyl-N, N-dimethylacetobetaine, preferably N—($C_8$-$C_{18}$)-acylaminopropyl-N,N-dimethylacetobetaine; ($C_{12}$-$C_{18}$)-alkyldimethylsulfopropylbetaine; amphoteric surfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g. ($C_{12}$-$C_{18}$)-alkyldimethylamine oxide, fatty acid amidoalkyldimethylamine oxide.

The proportion by weight of the amphoteric surfactants in the cosmetic, dermatological or pharmaceutical products according to the invention is prefereably in the range from 0.5 to 20% by weight, particularly preferably 1 to 10% by weight.

Furthermore, foam-boosting cosurfactants from the group consisting of alkylbetaines, alkylamidobetaines, aminopropionates, aminoglycinates, imidazoliniumbetaines and sulfobetaines, amine oxides and fatty acid alkanolamides or polyhydroxyamides, can be used in the cosmetic, dermatological or pharmaceutical products according to the invention.

Preferred surfactants in the cosmetic, dermatological or pharmaceutical products according to the invention are lauryl sulfate, laureth sulfate, cocoamidopropylbetaine, sodium cocoyl glutamate, disodium laureth sulfosuccinate and coconut fatty acid diethanolamide.

The cosmetic, dermatological or pharmaceutical products according to the invention can also comprise further additives customary in cosmetics, such as superfatting agents, stabilizers, biogenic active ingredients, glycerol, preservatives, pearlizing agents, dyes and fragrances, solvents, opacifiers, thickeners and dispersants, and also protein derivatives, such as gelatins, collagen hydrolyzates, natural- and synthetic-based polypeptides, egg yolk, lecithin, lanolin and lanolin derivatives, fatty alcohols, silicones, deodorizing agents, substances with a keratolytic and keratoplastic effect, enzymes and carrier substances. In addition, antimicrobially effective agents may be added to the cosmetic, dermatological or pharmaceutical products according to the invention.

Superfatting agents which may be used are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetylstearyl alcohol.

Stabilizers which may be used are metal salts of fatty acids, such as, for example, magnesium stearate, aluminum stearate and/or zinc stearate.

Biogenic active ingredients are understood as meaning, for example, plant extracts and vitamin complexes.

Suitable preservatives are, for example, phenoxyethanol, formaldehyde solution, parabens, pentanediol or sorbic acid.

Suitable pearlizing agents are, for example, glycol distearic esters, such as ethylene glycol distearate, but also fatty acid monoglycol esters.

Dyes that can be used are the substances approved and suitable for cosmetic purposes.

Suitable further thickeners are sodium chloride, potassium chloride, ammonium chloride, sodium sulfate, fatty acid alkylolamides, cellulose derivatives, for example hydroxyethylcellulose, guar gum, polyvinyl alcohol, polyvinylpyrrolidone, hydroxypropyl guar gum, starch and starch derivatives, and natural gums, carboxyvinyl polymers, for example Carbopol 934, 940, 941, 956, 980, 981,1342,1382, ethylene glycol esters of fatty acids having 14 to 22, particularly preferably 16 to 22, carbon atoms, in particular mono- and diethylene glycol stearate.

Preference is also given to stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl-($C_{12}$-$C_{22}$)-, in particular ($C_{16}$-$C_{18}$)-amidobenzoic acid and soluble salts thereof, N,N-di($C_{16}$-$C_{18}$)-amidobenzoic acid and derivatives thereof.

Based on the finished cosmetic, dermatological or pharmaceutical product, the dispersants are used in concentrations of preferably from 0.5 to 10% by weight, particularly preferably from 0.5 to 5% by weight, especially preferably from 1 to 4% by weight.

The desired viscosity of the cosmetic, dermatological or pharmaceutical products can be established by adding water and/or organic solvents or by adding a combination of organic solvents and thickeners.

In principle, suitable organic solvents are all mono- or polyhydric alcohols. Preference is given to using alcohols having 1 to 4 carbon atoms, such as ethanol, propanol, isopropanol, n-butanol, isobutanol and t-butanol.

Preference is further given to monohydric alcohols, particularly preferably those chosen from methanol, ethanol, propanol, isopropanol, n-butanol, isobutanol, t-butanol, hexyl alcohol, trimethylhexanol, butyloctanol, oleyl alcohol, benzyl alcohol, phenylpropanol and diacetone alcohol, especially preferably those having 1 to 6 carbon atoms, extraordinarily preferably methanol, ethanol, propanol, isopropanol, n-butanol, isobutanol and t-butanol.

Preference is also given to polyhydric alcohols and derivatives of polyhydric alcohols, particularly preferably those chosen from the group consisting of methoxyethanol, ethoxyethanol, butoxyethanol, isobutoxypropanol, methoxyisopropanol, butoxyisopropanol, phenoxyisopropanol, methoxybutanol, preferably 4-methoxybutanol, methoxymethylbutanol, glycol, benzene glycol, propylene glycol, butylene glycol, methylpropanediol, pentylene glycol, isopentyldiol, neopentyl glycol, hexylene glycol, hexanediol, ethylhexanediol, diethylene glycol, methoxy diglycol, ethoxy diglycol, butoxy diglycol, dimethoxy diglycol, dipropylene glycol, glycerol and 1,2,6-hexanetriol, very particularly preferably glycol, propylene glycol, butylene glycol and glycerol.

Preference is also given to ketones, esters, ethers, amides, sulfoxides, nitriles, O—, N— and S-heterocycles, preferably acetone, methoxyethanol acetate, triacetin (glycerol triacetate), amyl acetate, benzyl benzoate, benzyl laurate, butoxyethyl acetate, butyl acetate, butylene glycol propionate, butyl lactate, butyloctyl benzoate, butyloctyl salicylate, butyrolactone, $C_{5-18}$-fatty acid triglycerides, PEG/PPG copolymers (PEG: polyethylene glycol; PPG: polypropylene glycol), propyl acetate, propylene carbonate, propylene glycol butyl ether, propylene glycol propyl ether, tetrahydrofurfuryl acetate, tetrahydrofurfuryl alcohol, thiolanediol, tributyl citrate, tributylcresylbutane, acetonitrile, THF (tetrahydrofuran), DMF (dimethylformamide), DMSO (dimethyl sulfoxide), DBU (diazabicycloundecane), pyridine, particularly preferably acetone, acetonitrile, THF (tetrahydrofuran) and DMF (dimethylformamide).

Preference is also given to ethoxylated and/or propoxylated alcohols, particularly preferably ethoxylated and/or propoxylated alcohols having 1 to 40, preferably 1 to 30, particularly preferably 1 to 20, mol of ethylene oxide and/or propylene oxide, especially preferably ethoxylated and/or propoxylated alcohols chosen from polypropylene glycol-7 (PPG-7: on average containing 7 propylene glycol units), polypropylene glycol-10, PPG-2-buteth-3, PPG-3-buteth-5, PPG-5-buteth-7, PPG-7-buteth-10, PPG-12-buteth-16, PPG-15-buteth-20, PPG-20-buteth-20, PPG-2 butyl ether, PPG-3 butyl ether, PPG-24-glycereth-24, PPG-10 glyceryl ether, glyceryl ether, PPG-2 methyl ether, PPG-3 methyl ether, PPG-2 methyl ether acetate, PPG-2 propyl ether, propylene glycol butyl ether, propylene glycol propyl ether, methoxy PEG-10, methoxy PEG-16, buteth-3, sorbeth-6 and sorbeth-20.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

If the cosmetic, dermatological and pharmaceutical products according to the invention are emulsions, the nonaqueous fraction of the emulsions, which consists largely of the emulsifier, the thickener and the oil body, is usually 5 to 95%, preferably 15 to 75% by weight. From this it follows that the emulsions can comprise 5 to 95% by weight, and preferably 25 to 85% by weight of water depending on whether the intention is to produce lotions with a comparatively low viscosity, or creams and ointments with a high viscosity.

The emulsions can be used as skin care products, such as, for example, day creams, night creams, care creams, nutrient cream, body lotions, ointments and the like and comprise, as further auxiliaries and additives, oil bodies, coemulsifiers, superfatting agents, fats, waxes, stabilizers, biogenic active ingredients, glycerol, preservatives, dyes and fragrances.

Suitable oil bodies are, for example, Guerbet alcohols based on fatty alcohols having 6 to 18, preferably 8 to 10, carbon atoms, esters of linear ($C_6$-$C_{13}$)-fatty acids with linear ($C_6$-$C_{20}$)-fatty alcohols, esters of branched ($C_6$-$C_{13}$)-carboxylic acids with linear ($C_6$-$C_{20}$)-fatty alcohols, esters of linear ($C_6$-$C_{18}$)-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on ($C_6$-$C_{10}$)-fatty acids, vegetable oils, branched primary alcohols, substituted cyclohexanes, Guerbet carbonates, dialkyl ethers and/or aliphatic or aromatic hydrocarbons. The proportion of the oil bodies in the nonaqueous fraction of the emulsions can constitute 5 to 95% by weight and preferably 15 to 75% by weight.

Suitable nonionogenic coemulsifiers are, inter alia, addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol, and in particular polyglycerol, esters, such as, for example, polyglycerol polyricinoleate and polyglycerol poly-12-hydroxystearate. Likewise suitable are mixtures of compounds of two or more of these classes of substance.

Suitable ionogenic coemulsifiers are, for example, anionic emulsifiers, such as mono-, di- or triphosphoric esters, but also cationic emulsifiers, such as mono-, di- and tri-alkyl quats and polymeric derivatives thereof.

In order to adjust the rheological properties of aqueous or solvent-containing emulsions or suspensions, a large number of different systems are given in the specialist literature. For example, cellulose ethers and other cellulose derivatives (e.g. carboxymethylcellulose, hydroxyethylcellulose), gelatin, starch and starch derivatives, sodium alginates, fatty acid polyethylene glycol esters, agar agar, tragacanth or dextrins, are known. The synthetic polymers used are various materials, such as, for example, polyvinyl alcohols, polyacrylamides, polyvinylamides, polysulfonic acids, polyacrylic acid, polyacrylic esters, polyvinylpyrrolidone, polyvinyl methyl ether, polyethylene oxides, copolymers of maleic anhydride and vinyl methyl ether, and diverse mixtures and copolymers of the abovementioned compounds, including their various salts and esters. These polymers can, if desired, be crosslinked or uncrosslinked.

The emulsions can be prepared in a known manner, i.e. for example by hot, hot/cold or PIT emulsification.

EXAMPLE 1

The following washing lotion is prepared using the concentrate E from table 1.

|   |   | % by wt. |
|---|---|---|
| A | Hostapon ® KCG | 30.0 |
| B | Fragrance | 0.3 |
| C | Water | ad 100 |
|   | Concentrate E from Table 1 | 1.0 |
|   | Dye solution | 1.0 |
|   | Preservative | q.s. |
|   | Genagen ® CAB | 10.0 |

Preparation

Phase B is firstly dissolved into phase A. The components of phase C are then added one after the other to the solution.

The viscosity of the washing lotion is 6500 mPas (20° C., Brookfield viscometer, 20 rpm).

An analogous composition which differs merely in that it does not comprise the concentrate E from table 1 has a viscosity of only 25 mpas.

INCI name of the commercial products used:
Hostapon® KCG (Clariant) Sodium Cocoyl Glutamate
Genagen® CAB (Clariant) Cocamidopropyl Betaine

The invention claimed is:

1. A composition in liquid form comprising
a) 20 to 95 weight percent based on a total composition of at least one oxyalkylated polyglycerol ester of the formula (1)

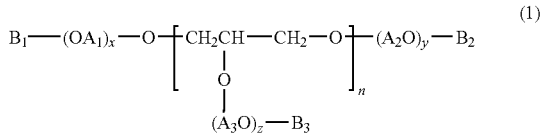

wherein
$A_1$, $A_2$ and
$A_3$ are —$C_2H_4$,
$B_1$, $B_2$ and
$B_3$ independently of one another are in each case hydrogen or a group of the formula —COR, where at least one of the radicals $B_1$, $B_2$ or $B_3$ is a group of the formula —COR,
R is $C_7$-$C_{21}$-alkyl,
n is on average a number from 1.8 to 5 and
x, y and z are numbers from 0 to 100, where the sum of x, y and z is 130 to 170,
b) an organic solvent or organic solvent mixture selected from the group consisting of:
PEG-6 caprylic/capric glycerides. a polyethylene glycol derivate of a mixture of mono-, di- and triglycerides of caprylic and capric acids with, on average, 6 mol of ethylene oxide and PEG-7 glyceryl cocoate, a polyethylene glycol ether of glyceryl cocoate with, on average, 7 mol of ethylene oxide per 1 mol of glycerol and mixtures thereof, and
c) water, wherein the weight ratio of water to organic solvent or organic solvent mixture is from 3:1 to 1:3.

2. A method for thickening surfactant-containing systems, said method comprising adding a thickener comprising the compound of claim 1 to the surfactant-containing systems.

3. A method for preparing a cosmetic, dermatological or pharmaceutical product, said method comprising adding the compound of claim 1 to the cosmetic, dermatological or pharmaceutical product.

4. A cosmetic, dermatological or pharmaceutical product comprising the liquid composition of claim 1.

5. The cosmetic, dermatological or pharmaceutical product as claimed in claim 4, which is a shampoo, shower bath, shower gel, foam bath, gel, a lotion, cream or ointment.

6. A composition according to claim 1, comprising
a) at least one oxyalkylated polyglycerol ester of the formula (1)

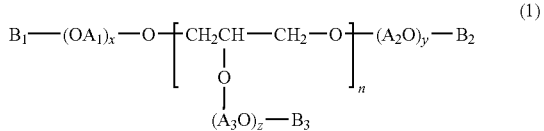

wherein
$A_1$, $A_2$ and
$A_3$ are —$C_2H_4$,
$B_1$, $B_2$ and
$B_3$ are independently of one another, a hydrogen or a stearoyl radical wherein at least one of the radicals $B_1$, $B_2$ or $B_3$ is a stearoyl radical,
n is 2, and
x, y and z are numbers from 0 to 100, where the sum of x, y and z is about 148.

7. A composition according to claim 1, wherein the organic solvent is selected from the group consisting of: PEG-6 caprylic/capric glycerides, polyethylene glycol derivates of a mixture of mono-, di- and triglycerides of caprylic and capric acids with, on average, 6 mol of ethylene oxide.

8. A composition in liquid form comprising
a) 30 to 95 weight percent based on a total composition of at least one oxyalkylated polyglycerol ester of the formula (1)

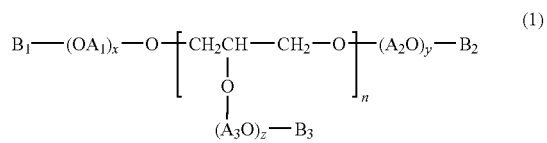

wherein
$A_1$, $A_2$ and
$A_3$ are —$C_2H_4$,
$B_1$, $B_2$ and
$B_3$ are independently of one another are in each case hydrogen or a group of the formula —COR, where at least one of the radicals $B_1$, $B_2$ or $B_3$ is a group of the formula —COR,
R is $C_7$-$C_{21}$-alkyl,
n is on average a number from 1.8 to 5, and
x, y and z are numbers from 0 to 100, where the sum of x, y and z is 130 to 170,
b) an organic solvent or organic solvent mixture selected from the group consisting of:
PEG-6 caprylic/capric glycerides, a polyethylene glycol derivate of a mixture of mono-, di- and triglycerides of caprylic and capric acids with, on average, 6 mol of ethylene oxide and PEG-7 glyceryl cocoate, a polyethylene glycol ether of glyceryl cocoate with, on average, 7 mol of ethylene oxide per 1 mol of glycerol and mixtures thereof, and
c) water, wherein the weight ratio of water to organic solvent or organic solvent mixture is from 3:1 to 1:3.

9. A composition in liquid form comprising
a) 20 to 95 weight percent based on a total composition of at least one oxyalkylated polyglycerol ester of the formula (1')

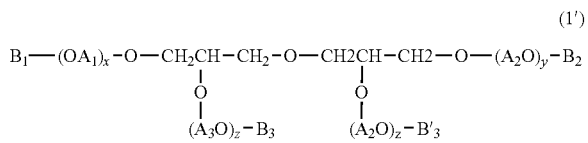

wherein
$A_1$, $A_2$ and
$A_3$ are —$C_2H_4$,
$B_1$, $B_2$, B3 and
$B'_3$ wherein exactly 1 of the 4 groups $B_1$, $B_2$, $B'_3$ is hydrogen, and the other 3 groups are stearoyl x, y and z are numbers from 0 to 100, where the sum of x, y and z is about 148 b) an organic solvent or organic solvent mixture selected from the group consisting of:

PEG-6 caprylic/capric glycerides, a polyethylene glycol derivate of a mixture of mono-, di- and triglycerides of caprylic and capric acids with, on average, 6 mol of ethylene oxide and PEG-7 glyceryl cocoate, a polyethylene glycol ether of glyceryl cocoate with, on average, 7 mol of ethylene oxide per 1 mol of glycerol and mixtures thereof, and c) water, wherein the weight ratio of water to organic solvent or organic solvent mixture is from 3:1 to 1:3.

* * * * *